US012188956B2

(12) United States Patent
Cheung et al.

(10) Patent No.: US 12,188,956 B2
(45) Date of Patent: Jan. 7, 2025

(54) METHOD AND SYSTEM FOR CHARACTERIZING, PREDICTING, AND OPTIMIZING MOVEMENTS OF COMPLEX SYSTEMS

(71) Applicant: Surge Motion Inc., Alhambra, CA (US)

(72) Inventors: Jeffrey Tai Kin Cheung, Fremont, CA (US); Derek T. Cheung, San Mateo, CA (US); Vicky L. Cheung, Portland, OR (US); Gary N. Jin, Portland, OR (US)

(73) Assignee: Surge Motion Inc., Fremont, CA (US)

( * ) Notice: Subject to any disclaimer, the term of this patent is extended or adjusted under 35 U.S.C. 154(b) by 776 days.

(21) Appl. No.: 16/592,584

(22) Filed: Oct. 3, 2019

(65) Prior Publication Data

US 2020/0110111 A1 Apr. 9, 2020

Related U.S. Application Data

(60) Provisional application No. 62/740,576, filed on Oct. 3, 2018.

(51) Int. Cl.
*G01P 13/00* (2006.01)
*A61B 5/00* (2006.01)
(Continued)

(52) U.S. Cl.
CPC ............ *G01P 13/00* (2013.01); *A61B 5/1114* (2013.01); *A61B 5/1126* (2013.01); *A61B 5/4866* (2013.01); *A61B 5/6823* (2013.01); *A61B 5/7257* (2013.01); *A61B 5/7278* (2013.01); *G01P 15/08* (2013.01); *G01P 15/14* (2013.01); *G01P 15/18* (2013.01); *G06V 40/25* (2022.01); *A61B 5/1117* (2013.01); *A61B 2562/0219* (2013.01); *A61B 2562/0223* (2013.01)

(58) Field of Classification Search
CPC .......... G01P 13/00; G01P 15/14; G01P 15/08; G01P 15/18; G06K 9/00348; A61B 5/6823; A61B 5/1114; A61B 5/1126; A61B 5/7257; A61B 5/7278; A61B 5/4866; A61B 5/1117; A61B 2562/0223; A61B 2562/0219
USPC ....................................................... 702/141
See application file for complete search history.

(56) References Cited

U.S. PATENT DOCUMENTS 10,307,086 B2 6/2019 Cheung
10,327,671 B2 6/2019 Cheung
(Continued)

*Primary Examiner* — Lee E Rodak
*Assistant Examiner* — Byung Ro Lee
(74) *Attorney, Agent, or Firm* — Shun Yao; Yao Legal Services, Inc.

(57) ABSTRACT

One embodiment provides a system for analyzing a motion of a complex system. During operation, the system obtains movement data associated with the motion over a time interval and computes, over the time interval, a distribution of energy associated with the motion based on the obtained movement data. The system further identifies energy peaks based on the distribution of the energy over the time interval, computes an energy-occurrence-frequency distribution based on the identified energy peaks over a predetermined energy range, and generates a motion-analysis result for the complex system based on the computed energy-occurrence-frequency distribution.

20 Claims, 10 Drawing Sheets

(51) Int. Cl.
*A61B 5/11* (2006.01)
*G01P 15/08* (2006.01)
*G01P 15/14* (2013.01)
*G01P 15/18* (2013.01)
*G06V 40/20* (2022.01)

(56) References Cited

U.S. PATENT DOCUMENTS

2013/0191034 A1* 7/2013 Weast .................... G01P 15/00
   702/19
2015/0164377 A1* 6/2015 Nathan ................ A61B 5/6802
   600/595

\* cited by examiner

METHOD AND SYSTEM FOR CHARACTERIZING, PREDICTING, AND OPTIMIZING MOVEMENTS OF COMPLEX SYSTEMS

RELATED APPLICATION

This application hereby claims priority under 35 U.S.C. § 119 to U.S. Provisional Patent Application No. 62/740,576, filed on 3 Oct. 2018, entitled "Characterizing, Predicting and Optimizing Movements of Complex Systems Using Energy Expenditure," by inventors Jeffery T. Cheung, Derek T. Cheung, Vicky L. Cheung, and Gary N. Jin.

BACKGROUND

Field of the Invention

This disclosure is generally related to motion analysis. More specifically, this disclosure is related to a method and a system that characterizes movements of a complex system based on its energy expenditures.

Related Art

Measuring and characterizing movements of a nonlinear, complex system (e.g., a human body or a machine) can be challenging due to the structural complexity of the system. Current approaches often rely on features associated with the magnitude, direction, and trajectory of a movement to characterize the movement. More specifically, these features can be measured, calculated, and described as force, acceleration, velocity, and displacement. However, obtaining accurate measurement of such features of a nonlinear, complex system can be very difficult. For example, traditional approaches to analyze human movements use an elaborate optoelectronic setup with multiple light-emitting diodes (LEDs) and reflective markers placed on various parts of the person under test. During test, high-speed cameras are used to capture sequential frames when the person is moving (e.g., walking or running). Information regarding the movements of the person can be extracted using a frame-by-frame analysis technique followed by complex computations. Such approaches are cumbersome, expensive, inefficient, and can only be performed offline (e.g., after the test is done).

SUMMARY

One embodiment provides a system for analyzing a motion of a complex system. During operation, the system obtains movement data associated with the motion over a time interval, and computes, over the time interval, a distribution of energy associated with the motion based on the obtained movement data. The system further identifies energy peaks based on the distribution of the energy over the time interval, computes an energy-occurrence-frequency distribution based on the identified energy peaks over a predetermined energy range, and generates a motion-analysis result for the complex system based on the computed energy-occurrence-frequency distribution.

In a variation on this embodiment, obtaining the movement data can include attaching a motion sensor substantially near a center of gravity of the complex system and obtaining outputs of the motion sensor. The motion sensor can include at least one of: a three-axis accelerometer, a gyroscope, and a magnetometer.

In a variation on this embodiment, computing the energy-occurrence-frequency distribution comprises one of: counting an occurrence of an energy peak having a unique energy value and counting an occurrence of an energy value between two identified energy peaks.

In a variation on this embodiment, the movement data can include acceleration data, and computing the distribution of the energy can include: performing a Fourier transform (FT) operation on the acceleration data to obtain a plurality of frequency components of the acceleration; computing, for each frequency of a predetermined set of frequencies, a frequency component of the energy; and summing the computed frequency components of the energy.

In a variation on this embodiment, the system further obtains an energy-occurrence-frequency distribution as a function of energy for a reference system.

In a further variation, generating the motion-analysis result can include selecting a reference energy-occurrence frequency and comparing energy values corresponding to the reference energy-occurrence frequency for the complex system and the reference system.

In a variation on this embodiment, generating the motion-analysis result can include one of: computing a stability factor based on a ratio between a count of energy occurrences for energies up to a reference energy value and a total count of energy occurrences, and computing a distance between upper and lower boundaries of the energy-occurrence-frequency distribution at a reference energy-occurrence frequency.

BRIEF DESCRIPTION OF THE FIGURES

In the figures, like reference numerals refer to the same figure elements.

DETAILED DESCRIPTION

Overview

Embodiments of the present invention provide a system and method for characterizing the motion of a complex system. During operation, the system computes energy expenditures of a complex system based on movement data obtained while the complex system is in motion. By observing the self-organized criticality (SoC) behavior of the complex system, the system can determine the stability of the system. More specifically, the motion of the complex system with the SoC behavior can be characterized by the occurrences of unique energy expenditure peak values (e.g., peaks of an energy distribution curve over a time interval) and their rate change. Increased occurrences of energy peaks having high energy values can indicate poor system stability.

Motion Characterization Based on Sensor Data

Figure 1:
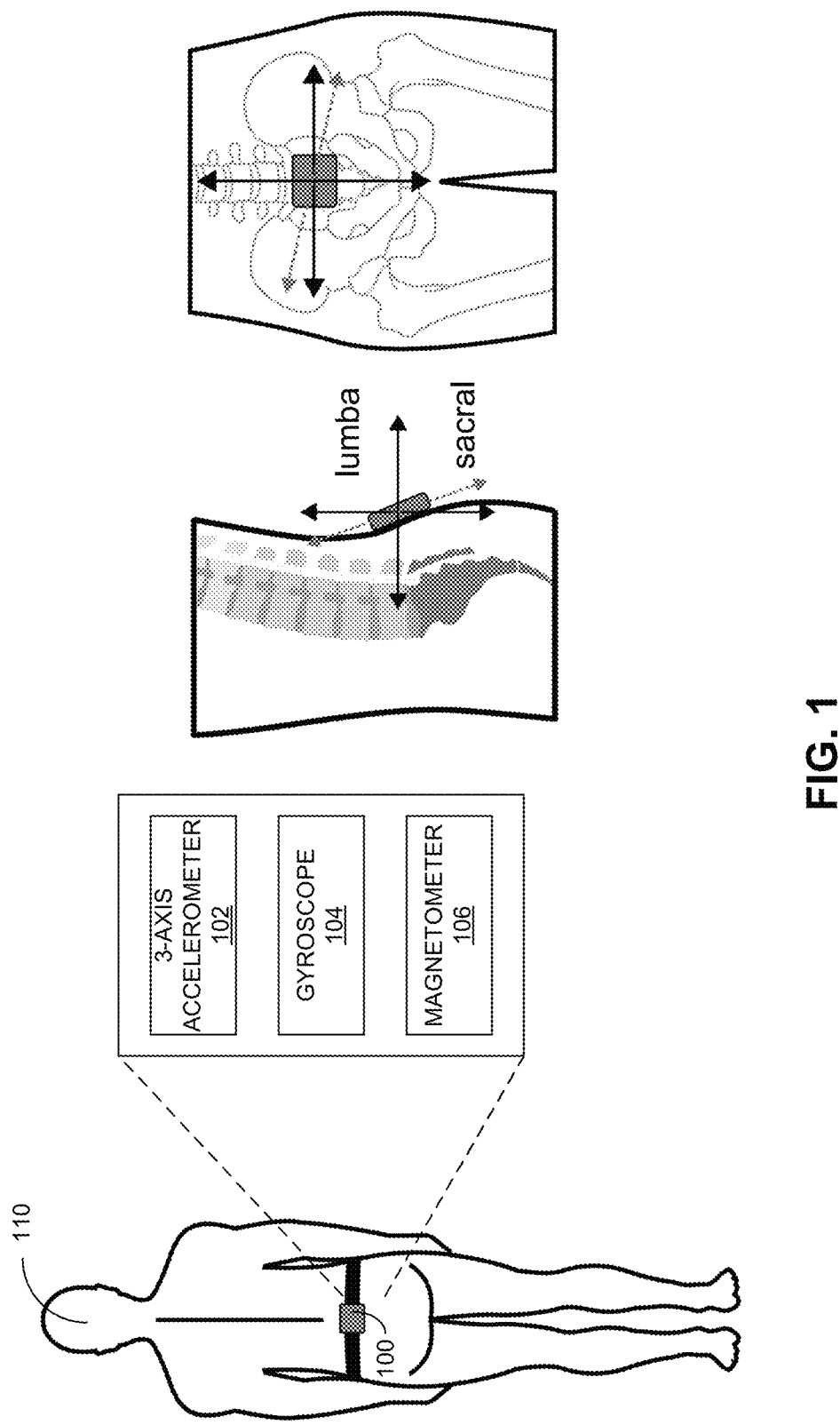
FIG. 1 illustrates a motion sensor mounted on a human body, according to one embodiment.

FIG. 1 illustrates a motion sensor mounted on a human body, according to one embodiment. In FIG. 1, motion sensor 100 can include at least a three-axis accelerometer 102, a gyroscope 104, and a magnetometer 106. Motion sensor 100 can record movements in all six-degrees of freedom, including three translations (surge, sway, and heave) and three rotations (roll, pitch, and yaw). Note that surge refers to the forward-and-backward motion (along the X-axis), sway refers to the left-and-right motion (along the Y-axis), and heave refers to the up-and-down motion (along the Z-axis); whereas roll refers to tilting side-to-side on the X-axis, pitch refers to tilting forward-and-backward on the Y-axis, and yaw refers to turning left-and-right on the Z-axis.

FIG. 1 shows that motion sensor 100 is mounted on the lower back of user 110. More specifically, motion sensor 100 can be placed directly behind the lumbosacral joint of user 110, as shown in more details by the two drawings on the right side of FIG. 1. Various mounting mechanisms can be used to mount motion sensor 100 on user 110, including but not limited to: attaching to a belt, clipping onto an item of clothing, taping directly onto the body, etc. It is not necessary that motion sensor 100 maintains an upward orientation; the system can detect and compensate for the tilt of motion sensor 100.

During measurement, user 110 can stand still or perform a required movement (e.g., walking, running, swimming, pedaling a bike) for a predetermined duration. Note that, although user 110 is standing still, he is still considered to be in motion, because a person's body typically makes small movements (e.g., swaying) while attempting to stand still. The sampling rate of motion sensor 100 can be between a few hertz and a few thousand hertz. In some embodiments, the sampling rate can be roughly 100 Hz. The sensor data can be processed in real time. In alternative embodiments, the sensor data can be processed offline.

During measurement, user 110 can perform a required movement (e.g., walking, running, swimming, pedaling a bike) for a predetermined duration and outputs of the various modules of motion sensor 100 can be recorded. The sampling rate of motion sensor 100 can be between a few hertz and a few thousand hertz, as long as the sampling rate is sufficient to record changes of the movement. A motion that changes rapidly (e.g., a high speed rotation) will require motion sensor 100 to have a higher sampling rate. In some embodiments, the sampling rate can be roughly 100 Hz. The sensor data can be processed in real time. In alternative embodiments, the sensor data can be processed offline.

Figure 2:
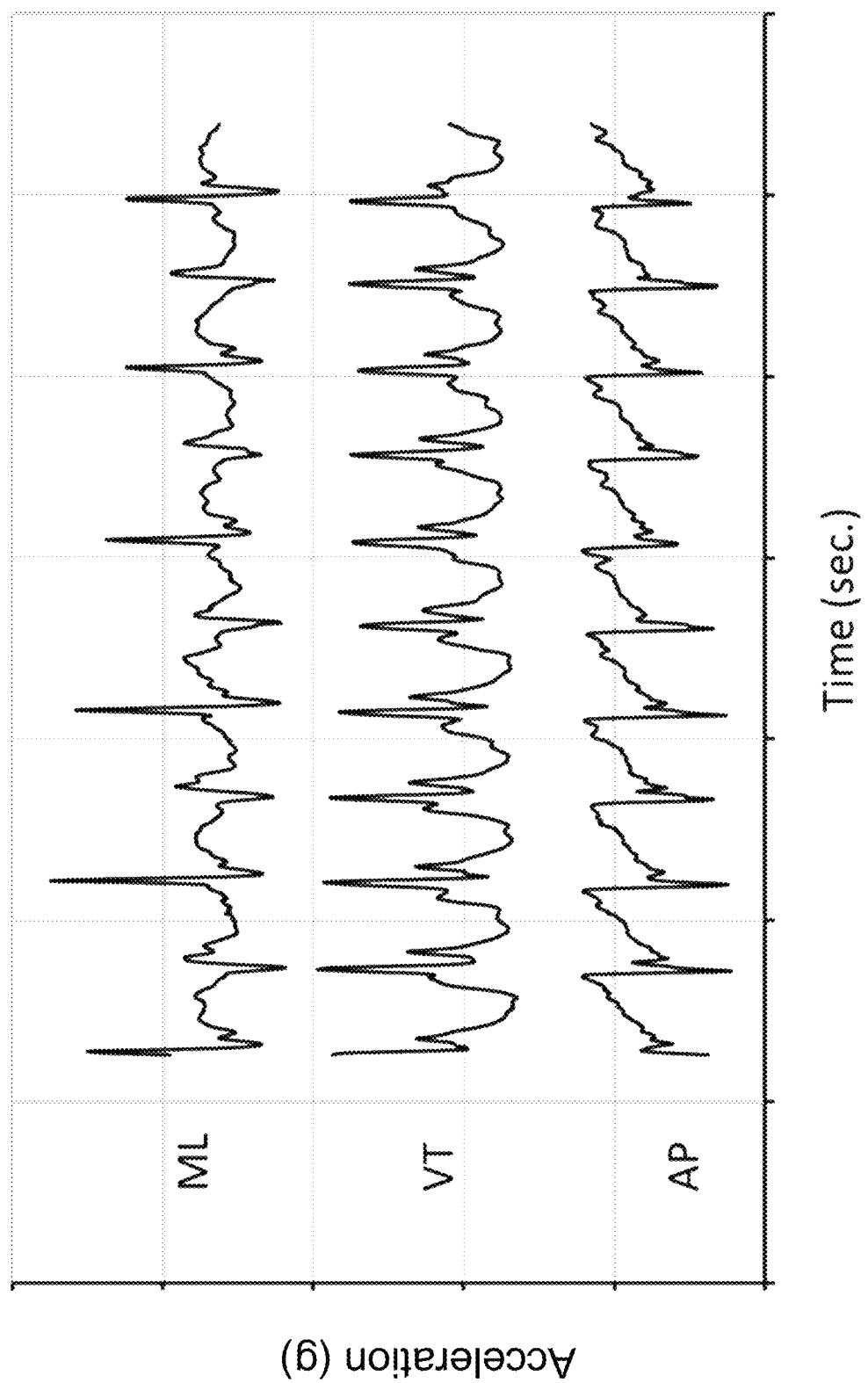
FIG. 2 illustrates exemplary acceleration data, according to one embodiment.

Raw sensor data can include time-dependent acceleration data along with rotational gyro data, which can be separately processed. FIG. 2 illustrates exemplary acceleration data, according to one embodiment. The acceleration data can be obtained along the three orthogonal directions: Medial Lateral (or sway) $A(t)_{ML}$, Vertical (or heave) $A(t)_{VT}$, and Anterior Posterior (or surge) $A(t)_{AP}$. Various types of information associated with the movement of a complex system can be derived from the sensor data.

Conventional approaches for analyzing the motion of a complex system are mostly concerned with measuring the magnitude (e.g., the acceleration and speed), direction, and trajectory (e.g., the displacement over time) of the motion. Although such measurements can provide information regarding certain aspects of the motion, they often fail to provide a general description regarding the complex system as a whole. For example, the acceleration and speed information may not be used to infer information regarding the stability of the complex system.

In contrast, embodiments of the present invention develop a motion-stability criterion that can be used to describe the motion of a complex system. Because a complex system can exhibit SOC behaviors in terms of its energy expenditure during a motion, one can use such SOC properties to derive the motion-stability criterion. SOC is a property of dynamical systems to organize its microscopic behavior to be spatial (and/or temporal) scale independent. SOC is typically observed in slowly-driven non-equilibrium systems with extended degrees of freedom and a high level of non-linearity (e.g., a human in motion or a running car engine). For example, when a person is standing still on a hard surface and tries to maintain his balance, his body can make tiny movements in the horizontal plane. More specifically, his body can sway back-and-forth (i.e., in the anterior posterior (AP) direction) and left-and-right (i.e., in the medial lateral (ML) direction). Such a sway motion can exhibit an SOC behavior. More particularly, the energy expenditure associated with the motion (e.g., the amount of kinetic energy included in the motion) may exhibit a certain SOC behavior and characteristics extracted from such an SOC behavior can be used to characterize the motion of the complex system. In the particular example of a person maintaining balance, characteristics extracted from the SOC behavior can also be used to make a determination regarding the health, wellness, fitness level, and/or age of the person. For example, such characteristics can be used to estimate an individual's age, evaluate the individual's risk of falling, or diagnosing the individual of having a certain disease (e.g., Parkinson's, etc).

The energy involved in a motion of a complex system (e.g., a person who is standing still, walking, running, swimming, or riding a bike; a car that is running; a plane in air, a wind turbine that is rotating, etc.) can be decomposed into two portions, the non-oscillatory motion energy portion and the oscillatory motion energy portion. The non-oscillatory motion energy is the amount of energy included in the intended motion of the system, whereas the oscillatory motion energy is the amount of energy included in the unintended motion, which is oscillatory in nature. For example, for a person standing still, the amount of energy included in the intended motion (i.e., standing still) can be zero, whereas the amount of energy included in the unintended motion (i.e., body swaying) can be non-zero. On the other hand, for a person walking on a flat surface, both the amounts of energy included in the intended motion (i.e., the forward motion) and the unintended motion (i.e., body swaying) can be non-zero. Similarly, for a rotating wind turbine, both the amounts of energy included in the intended motion (i.e., rotation) and the unintended motion (i.e., slightly off-axis vibrations) can be non-zero. Note that, although in certain scenarios, the intended motion itself can be oscillatory in nature (e.g., the rotating of a wind turbine or the swinging of a pendulum), the energy included in such a motion can still be referred to as the non-oscillatory motion energy. The oscillatory motion energy is a special term used in this disclosure to refer to the energy include in the unintended, balance-keeping movements of a complex system.

The amount of the oscillatory energy in a motion is typically much smaller than the amount of the non-oscillatory energy in the motion. Using walking as an example, the amplitude of the oscillatory motion (e.g., the sway and the bouncing up and down of the body) can be about 10 times smaller than the stride length (e.g., 5 cm vs. 50 cm). As a result, the oscillatory motion energy can be 100 times smaller than the non-oscillatory motion energy. However, despite such a large disparity in magnitude, the oscillatory motion energy can provide important information associated with the movements. For example, a larger amount of oscillatory motion energy can be an indicator of an unstable system or motion.

In some embodiments, the oscillatory motion energy can be calculated from the raw acceleration data. More specifically, one can first transform the raw time-domain acceleration data into the frequency domain (e.g., by performing a Fourier transform operation), where:

$$A(t)_{ML} = a_{ML1}e^{i\omega ML1 t} + a_{ML2}e^{i\omega ML2 t} + a_{M3}e^{i\omega ML3 t} + \ldots,$$

$$A(t)_{VT} = a_{VT1}e^{i\omega VT1 t} + a_{VT2}e^{i\omega VT2 t} + a_{VT3}e^{i\omega VT3 t} + \ldots, \text{ and}$$

$$A(t)_{AP} = a_{AP1}e^{i\omega AP1 t} + a_{AP2}e^{i\omega AP2 t} + a_{AP3}e^{i\omega AP3 t} + \ldots,$$

where $a_i$ is the amplitude for each frequency (e.g., $\omega_i$) component.

The displacement X (t) can be computed by integrating the acceleration function twice: $X(t) = \iint A(t)dt$. Therefore, for each frequency component, the displacement is $$X_i(t) = -\frac{a_i}{\omega_i^2}e^{i\omega_i t}.$$

The oscillatory motion energy in the three orthogonal axes can be computed based on the displacement vectors. In some embodiments, the oscillatory motion energy in the three orthogonal axes can be computed using the following expressions:

$$E_{ML} = \frac{m}{8\pi^2}\left[\left(\frac{a_{ML1}}{f_{ML1}}\right)^2 + \left(\frac{a_{ML2}}{f_{ML2}}\right)^2 + \left(\frac{a_{ML3}}{f_{ML3}}\right)^2 + \ldots\right],$$

$$E_{VT} = \frac{m}{8\pi^2}\left[\left(\frac{a_{VT1}}{f_{V1}}\right)^2 + \left(\frac{a_{VT2}}{f_{V2}}\right)^2 + \left(\frac{a_{VT3}}{f_{V3}}\right)^2 + \ldots\right], \text{ and}$$

$$E_{AP} = \frac{m}{8\pi^2}\left[\left(\frac{a_{AP1}}{f_{AP1}}\right)^2 + \left(\frac{a_{AP2}}{f_{AP2}}\right)^2 + \left(\frac{a_{AP3}}{f_{AP3}}\right)^2 + \ldots\right].$$

Note that $E_{ML}$ is the amount of oscillatory motion energy in the medial lateral (ML) direction, $E_{VT}$ is the amount of oscillatory motion energy in the vertical (VT) direction, and $E_{AP}$ is the amount of oscillatory motion energy in the anterior posterior (AP) direction. The total amount of oscillation motion energy can be calculated as:

$$E_{Total} = E_{ML} + E_{VT} + E_{AP}.$$

In some embodiments, to compute the energy expenditure over a predetermined time interval, the system can convert the time-domain accelerate data for the time interval to the frequency domain by performing a Fourier transform (FT) operation (e.g., a fast FT (FFT) operation). The FFT operation can be performed for each direction, including the ML, VT, and AP directions. The system then computes the amount of oscillatory energy in each direction. Note that the oscillatory energy can be computed as a summation of all frequency components. However, because the amplitude for each frequency component is proportional to $1/f^2$, the contribution from the higher frequency components can be negligible. In some embodiments, when computing the oscillatory energy involved in the motion, the system sums up the frequency components up to a predetermined frequency (e.g., 10 or 20 Hz, depending on the application). This can reduce the computation complexity without significantly sacrificing accuracy. The oscillatory energy for each direction can be combined to obtain the total oscillatory energy consumed in the time interval.

In some embodiments, calculating the oscillatory energy in a motion can be performed in the time domain. More specifically, the energy expenditure of a motion over a predetermined time interval can be calculated based on the time-domain acceleration data. Moreover, depending on the type of motion, the energy expenditure can also be measured and calculated using other known methods. For example, it can be calculated based on system parameters, such as heart rate, muscle activation, fuel consumption, electrical power consumption, etc.

Figure 3:
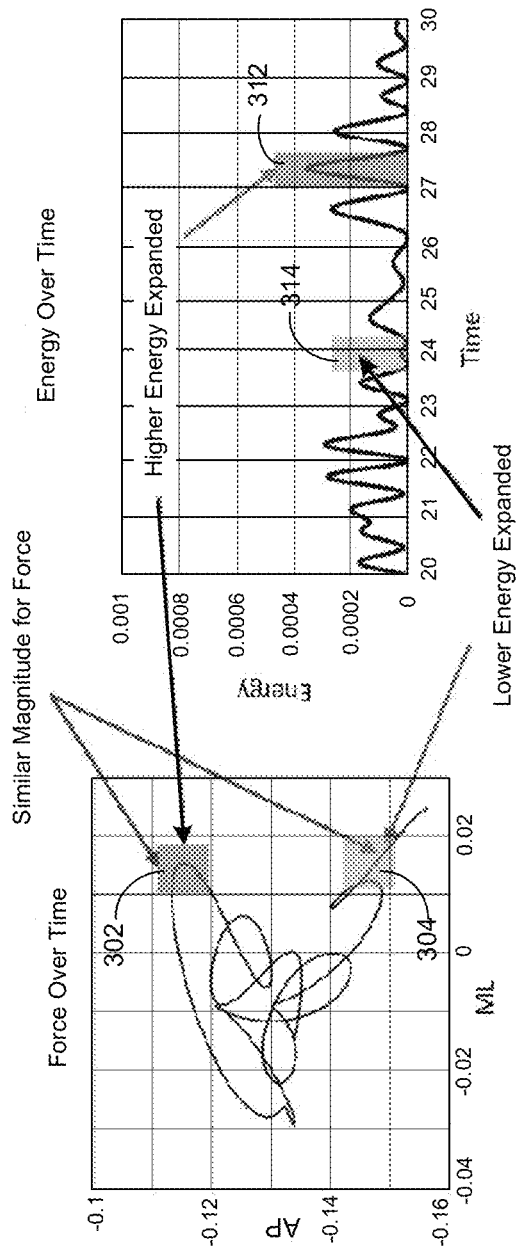
FIG. 3 illustrates an exemplary corresponding relationship between measured force and computed energy, according to one embodiment.

FIG. 3 illustrates an exemplary corresponding relationship between the measured force and the computed energy, according to one embodiment. In this example, the subject under test is a person standing still with a motion sensor mounted at his lower back. The left drawing of FIG. 3 shows the trajectory of the force over a predetermined time interval (e.g., 30 seconds) by plotting the force in the AP direction against the force in the ML direction. Note that, because the force is proportional to the acceleration, the trajectory of the force can be similar to the trajectory of the acceleration. In FIG. 3, forces in the two marked regions (regions 302 and 304) in the force trajectory can have similar magnitudes.

The right drawing of FIG. 3 shows the energy variation over the same predetermined time interval. As one can see from this energy-time plot, the energy oscillates in the time domain and the energy peaks can have different magnitudes. Marked regions 312 and 314 in the energy-time plot correspond to regions 302 and 304, respectively, in the force trajectory. One can see that although the forces in regions 302 and 304 have similar magnitudes, the energy levels corresponding to these forces can be significantly different. By correlating, referencing, and synchronizing the movement trajectory (e.g., the force or displacement trajectory) with the distribution of the energy expenditure, one can obtain various types of useful information regarding the complex system. In the example shown in FIG. 3, the corresponding relationship between the force trajectory and the energy-time plot can be used to predict the likelihood of a person falling and the likelihood direction of the fall. For example, for a particular time instant, the possibility of a person falling may be positively correlated with the magnitude of the force and the energy. The person may be at risk of falling if both the force magnitude and the energy exceed their predetermined thresholds. Such information can also be used to determine the body part (e.g., a foot, a leg, a knee, etc.) that causes the fall by identifying the body part (e.g., by attaching separate motion sensors) that contributes most to the increased force magnitude and energy.

Figure 4A:
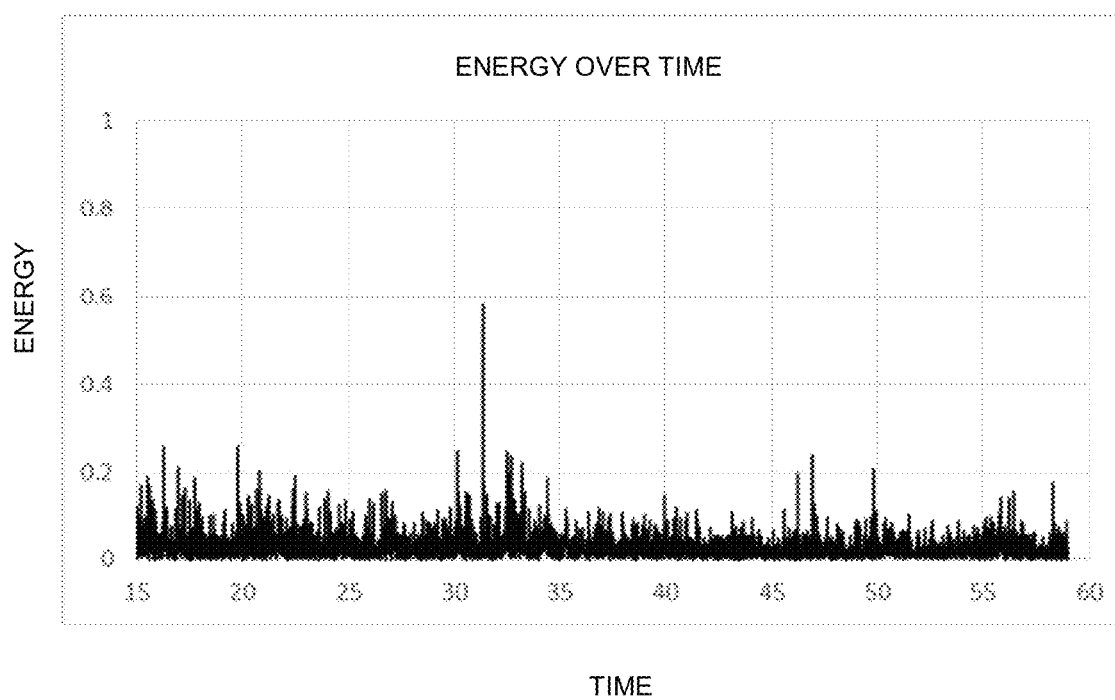
FIG. 4A illustrates an exemplary energy-time plot of a complex system, according to one embodiment.
Figure 4B:
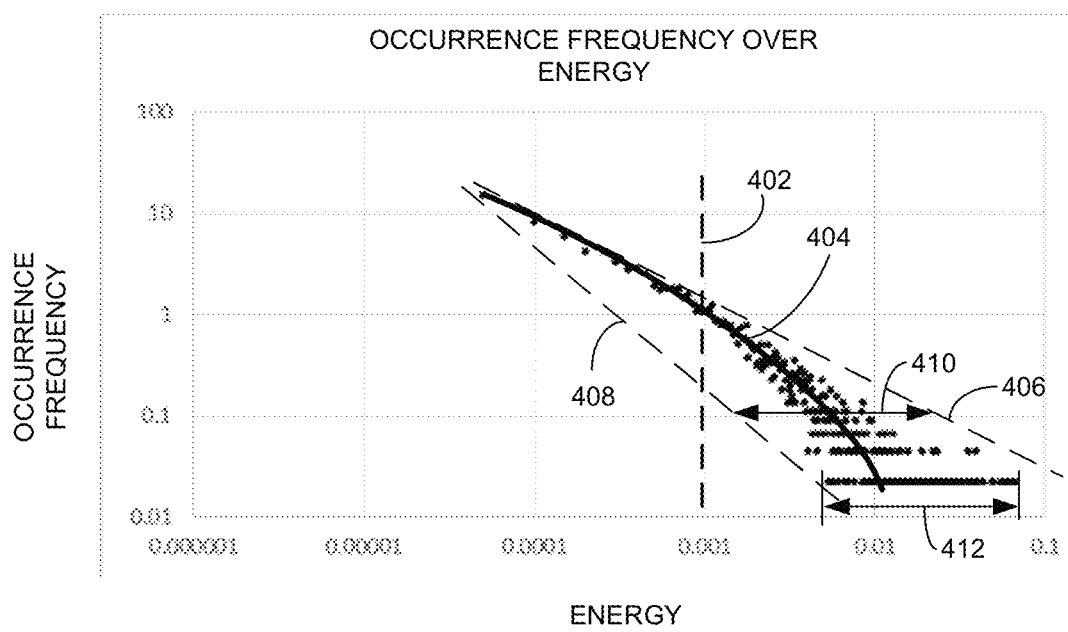
FIG. 4B plots the energy-peak-occurrence frequency as a function of the energy, according to one embodiment.

As discussed previously, a complex and nonlinear system (e.g., a human body) can exhibit SoC behavior. More specifically, the motion of a complex system with the SoC behavior can be described by the occurrences of unique energy peaks and the rate change of these occurrences. FIG. 4A illustrates an exemplary energy-time plot of a complex system, according to one embodiment. FIG. 4A can be similar to the right drawing of FIG. 3. However, FIG. 4A shows the energy distribution over a much longer time interval. The energy values can be similarly calculated based on data obtained from a motion sensor (e.g., an accelerometer). FIG. 4B plots the energy-peak-occurrence frequency as a function of the energy, according to one embodiment. In FIG. 4B, the X-axis is the energy level of energy peaks, and the Y-axis is the occurrence frequency of energy peaks of a particular energy level. In some embodiments, the system can examine the energy peaks in FIG. 4A and count the number of peaks for a particular energy level. FIG. 4B is plotted using logarithmic (log) scales for both the occurrence frequency and the energy. In FIG. 4B, the dots are data points obtained from the computed energy peaks. Dashed line 402 marks a cut-off point. Solid line 404 is a curve that fits the data points. Dashed lines 406 and 408 are the upper and lower boundaries of the data points.

In alternative amendments, instead of counting the occurrences of the energy peaks, one can count the occurrences of energy values between the identified peaks in the energy-time distribution. For example, if energy peaks $P_1$, $P_2$, and $P_3$ are identified, the occurrences of the energy values falling between energy values of peaks $P_1$ and $P_2$ can be counted. Similarly, the occurrences of the energy values falling between peaks $P_2$ and $P_3$ can also counted. The occurrence frequency of these energy values can be plotted to obtain the occurrence-frequency-over-energy curve.

From FIGS. 4A and 4B one can see that the number of counts of the low-energy peaks can be much higher than that of the high-energy peaks. In fact, the SOC of the complex system can be described using power laws. For a typical system with SOC behavior, the number of events D as a function of its size s is given by: $D(s)=As^{-\alpha}$, where A is a constant and $\alpha$ is the exponent describing statistical features of a SOC state. For a particular type of event (e.g., the occurrence of the energy peak in a motion), $\alpha$ remains unchanged. When plotted in the log scale, the SOC of the system can be described using a straight line, where $\alpha$ is the slope. From FIG. 4B, one can see that the oscillatory motion of the complex system exhibits the power-law SOC up to a certain cut-off value, as indicated by dashed line 402. When the energy level is above the cut-off value, the power law no longer holds true. More specifically, solid line 404 that fits the measured data points is no longer a straight line, as shown in FIG. 4B.

In some embodiments, one can derive information regarding the motion of a complex system from the SOC behavior of the oscillatory energy. More particularly, the occurrence-frequency-over-energy curve can provide various types of information, such as stability, symmetry, quality, and efficiency of the motion of a complex system. For example, when a complex system becomes less stable, the occurrence-frequency-over-energy curve can shift to the right, with an increased SOC cut-off value.

In addition to the amount of shift of the occurrence-frequency-over-energy curve, the distance between the upper and lower boundaries of the occurrence-frequency-over-energy curve (i.e., between dashed lines 406 and 408) can also be used to gauge the quality (e.g., stability and efficiency) of the motion. In general, a less noisy system (e.g., a more stable motion) can result in smaller energy differences among the energy peaks and, hence, a smaller distance between the upper and lower boundaries of the occurrence-frequency-over-energy curve. On the other hand, a noisier or less stable system can cause the energy peaks to have large variations, which can then lead to a larger distance between the upper and lower boundaries of the occurrence-frequency-over-energy curve. In some embodiments, such a distance can be measured at a selected reference occurrence frequency, such as the distance indicated by double arrow 410 shown in FIG. 4B. Alternatively, the upper and lower boundaries may not be straight lines, and the distance can be defined by the difference between a maximum energy value and a minimum energy value corresponding to a selected reference occurrence frequency, as illustrated by double arrow 412 in FIG. 4B.

Figure 5A:
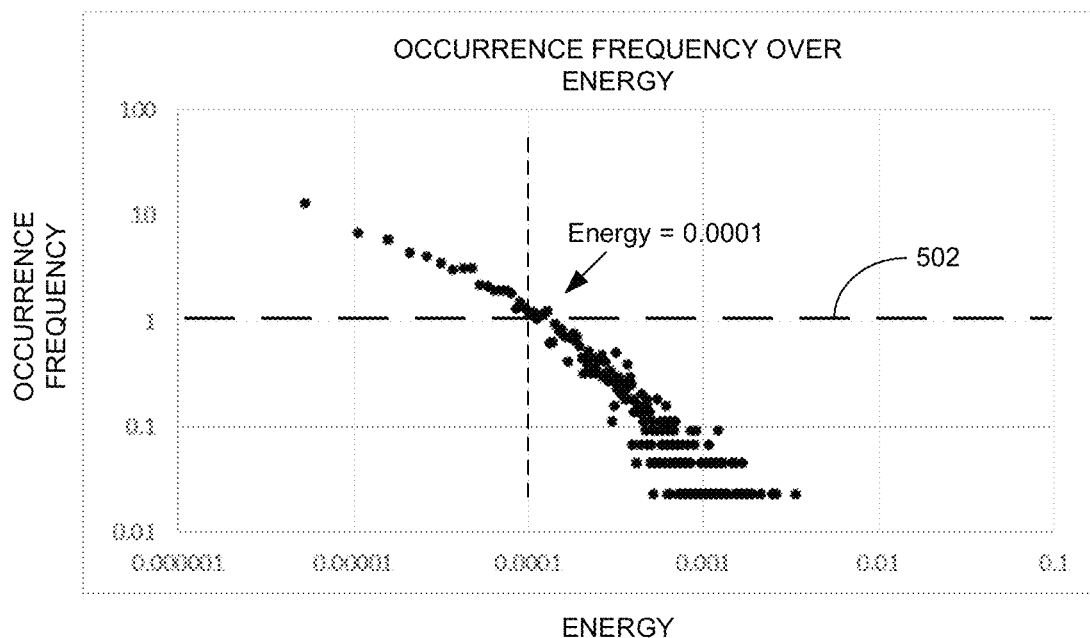
FIG. 5A shows the energy-peak-occurrence frequency as a function of the energy for a reference system, according to one embodiment.
Figure 5B:
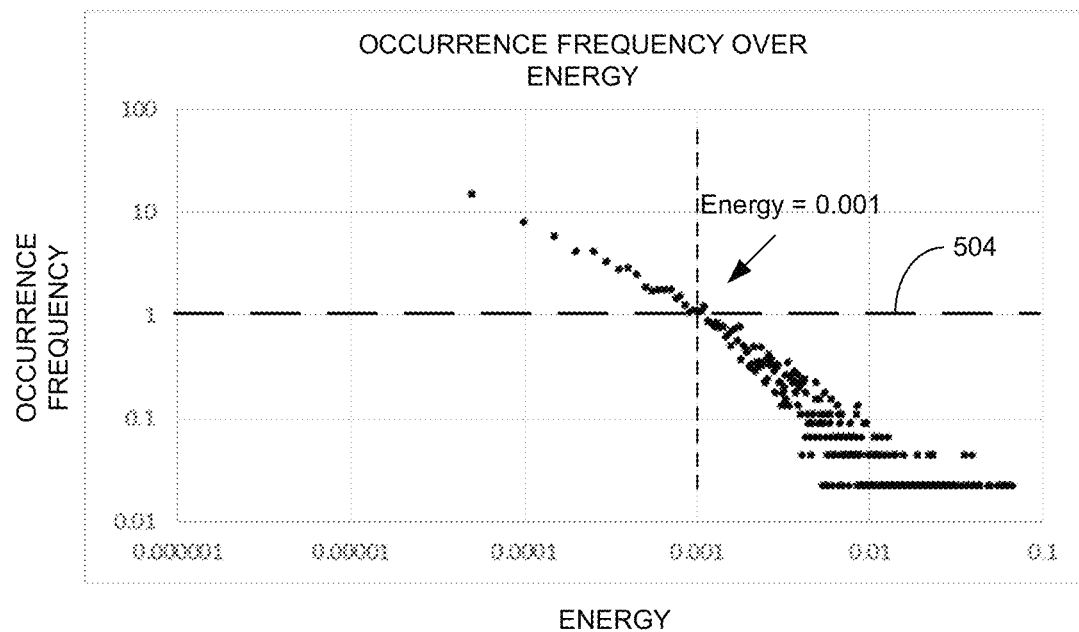
FIG. 5B shows the energy-peak-occurrence frequency as a function of the energy for an exemplary complex system, according to one embodiment.

FIG. 5A shows the energy-peak-occurrence frequency as a function of the energy for a reference system, according to one embodiment. More specifically, FIG. 5A can be generated using data collected from a reference object that remain still (e.g., by directly placing the motion sensor on a flat surface). FIG. 5B shows the energy-peak-occurrence frequency as a function of the energy for an exemplary complex system, according to one embodiment. In this example, the complex system is a human being, who is trying to remain balance while standing still. As discussed before, while trying to remain balance, the person's body sways, making small movements in the horizontal plane. Energies for such movements can be calculated and energy peaks can be counted. The occurrences of the energy peaks can then be plotted against the energy.

By comparing FIGS. 5A and 5B one can see that, compared to the reference system, the occurrence-frequency-over-energy curve for the person under test moves laterally to the right, indicating that the person is much less stable than the reference system. In this example, the individual is middle age and the occurrence-frequency-over-energy curve shifts moderately to the right. Experimental data have also shown that the occurrence-frequency-over-energy curve for a younger individual shifts to the right by a lesser amount and that the occurrence-frequency-over-energy curve for an older individual shifts a greater amount. This is because older individuals tend to wobble more when they stand, whereas younger individuals tend to be more stable. Similarly, the occurrence-frequency-over-energy curve for healthy individuals may move less to the right than that of individuals having health problems. In other words, the occurrence-frequency-over-energy curve can be a good indicator of a person's health, wellness, age, fitness level, etc. Hence, by obtaining and analyzing the oscillatory energy associated with the motion of a complex system, one can obtain various types of information that can be used to assess the quality (e.g., stability, symmetry, efficiency, etc.) of the motion.

In some embodiments, analyzing the oscillatory energy can involve comparing intersection points of the occurrence-frequency-over-energy curve at a reference occurrence value between the reference system and the system under test. More specifically, one can first determine a reference energy-peak-occurrence frequency based on various parameters, including but not limited to: the background noise level of the motion sensor, known optimal ranges of the complex system under test, and certain known threshold values. FIGS. 5A and 5B illustrate that a reference occurrence frequency (ROF) is chosen as 1. A straight line representing the equation ROF=1 is shown as dashed lines 502 and 504 in FIGS. 5A and 5B, respectively. In FIG. 5A, the intersection point between the occurrence-frequency-over-energy curve and dashed line 502 corresponds to an energy level of 0.0001. In FIG. 5B, the intersection point between the occurrence-frequency-over-energy curve and dashed line 504 corresponds to an energy level of 0.001. Note that, by comparing the energy level at the intersection points (e.g., whether the energy level of the system under test is greater, equal to, or less than that of the reference system), one can determine the relative motion quality of the system under test with respect to the reference system. For example, if the energy level of the system under test is greater than that of the reference system, the system under test is less stable than the reference system, and vice versa.

Figure 6A:
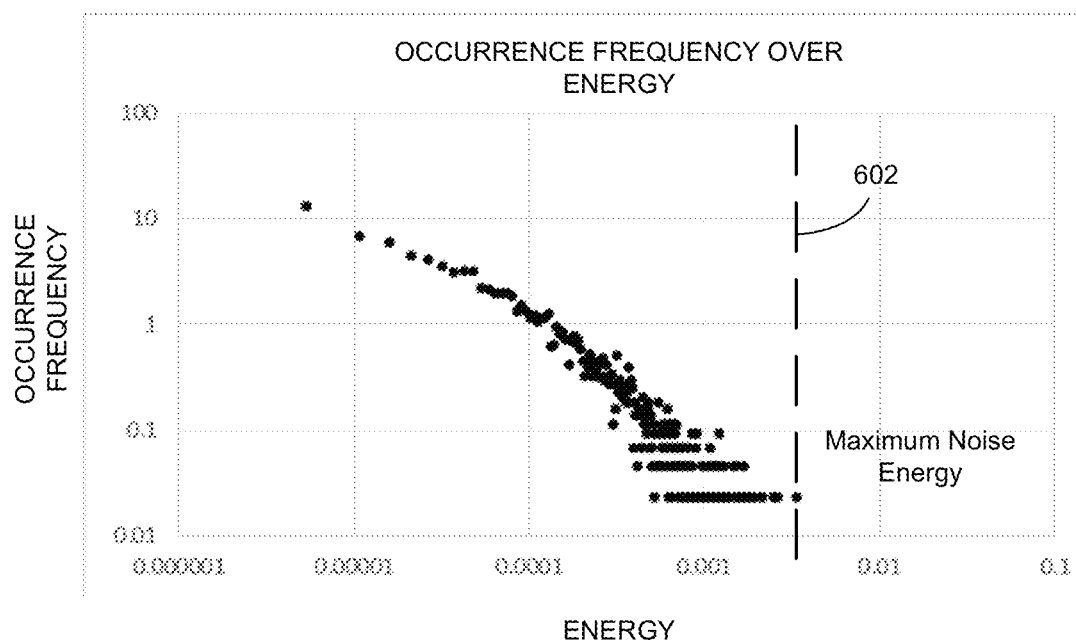
FIG. 6A shows the occurrence-frequency-over-energy curve of a reference system, according to one embodiment.
Figure 6B:
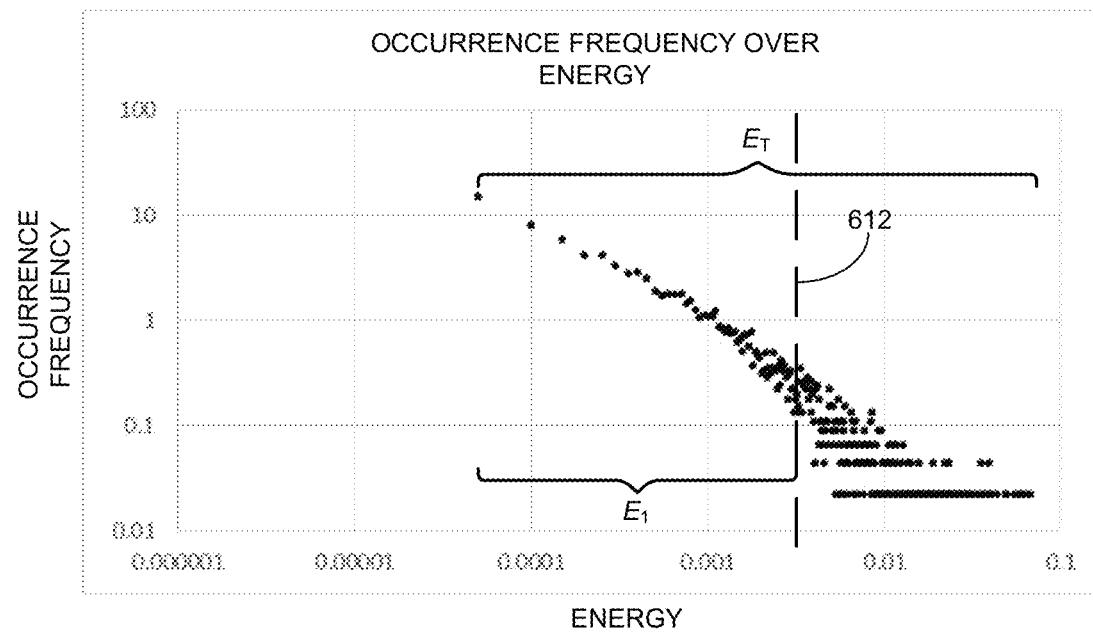
FIG. 6B shows the occurrence-frequency-over-energy curve of a system under test, according to one embodiment.

In some embodiments, analyzing the oscillatory energy can involve computing a stability index. More specifically, the stability index can be computed based on the relative amount of shift between the occurrence-frequency-over-energy curves of a reference system and the system under test. More specifically, one can obtain a reference energy value based on various parameters, including but not limited to: the background noise level of the motion sensor, known optimal ranges of the complex system under test, and certain known threshold values. FIG. 6A shows the occurrence-frequency-over-energy curve of a reference system, according to one embodiment. FIG. 6B shows the occurrence-frequency-over-energy curve of a system under test, according to one embodiment. In some embodiments, a reference energy value can be determined based on the maximum value of the energy peaks of the reference system. In this example, the reference system is the sensor itself. Therefore, the maximum energy peak value corresponds to the maximum sensor noise. In FIG. 6A, the maximum energy peak value can be marked by dashed line 602 and is used as a reference energy value. In FIG. 6B, the reference energy value is marked by dashed line 612. FIG. 6B also demonstrates that a count of energy peak occurrences up to the reference energy value can be marked $E_1$, and the total count of energy peak occurrences for the complex system can be marked $E_T$. In some embodiments, a stability index can be defined as: $100 \times E_1/E_T$. As one can see from FIGS. 6A and 6B, if there is no shift between the occurrence-frequency-over-energy curves of the reference system and the system under test (i.e., the reference energy value is also the maximum energy peak value for the system under test), then $E_1=E_T$. Consequently, the stability index can be 100. On the other hand, if the occurrence-frequency-over-energy curve of the system under test is shifted significantly to the right such that the minimum energy peak value of the system under test is larger than the maximum sensor noise energy, $E_1=0$ and the stability index is zero.

In addition to relying on the reference occurrence frequency or the reference energy value, in some embodiments, the system can compute the SOC cut-off value (i.e., the energy value beyond which the power law of the SOC starts to fail). More specifically, to compute the SOC cut-off value, the system can monitor the change of slope of the occurrence-frequency-over-energy curve. In other words, the system can monitor the rate of change (in the log scale) of the occurrence frequency. When the system is in the SOC "zone" (i.e., when the SOC power law is valid), the slope of the occurrence-frequency-over-energy curve remains a constant. However, when the system is no longer in the SOC zone, the slope changes. Therefore, by monitoring the slope change (e.g., by determining whether the change of the slope is greater than a predetermined threshold), the system can determine the cut-off energy value. When the occurrence-frequency-over-energy curve shifts to the right, the SOC cut-off value increases. A complex system having a larger cut-off energy value is less stable than a complex system having a smaller cut-off energy value.

Figure 7:
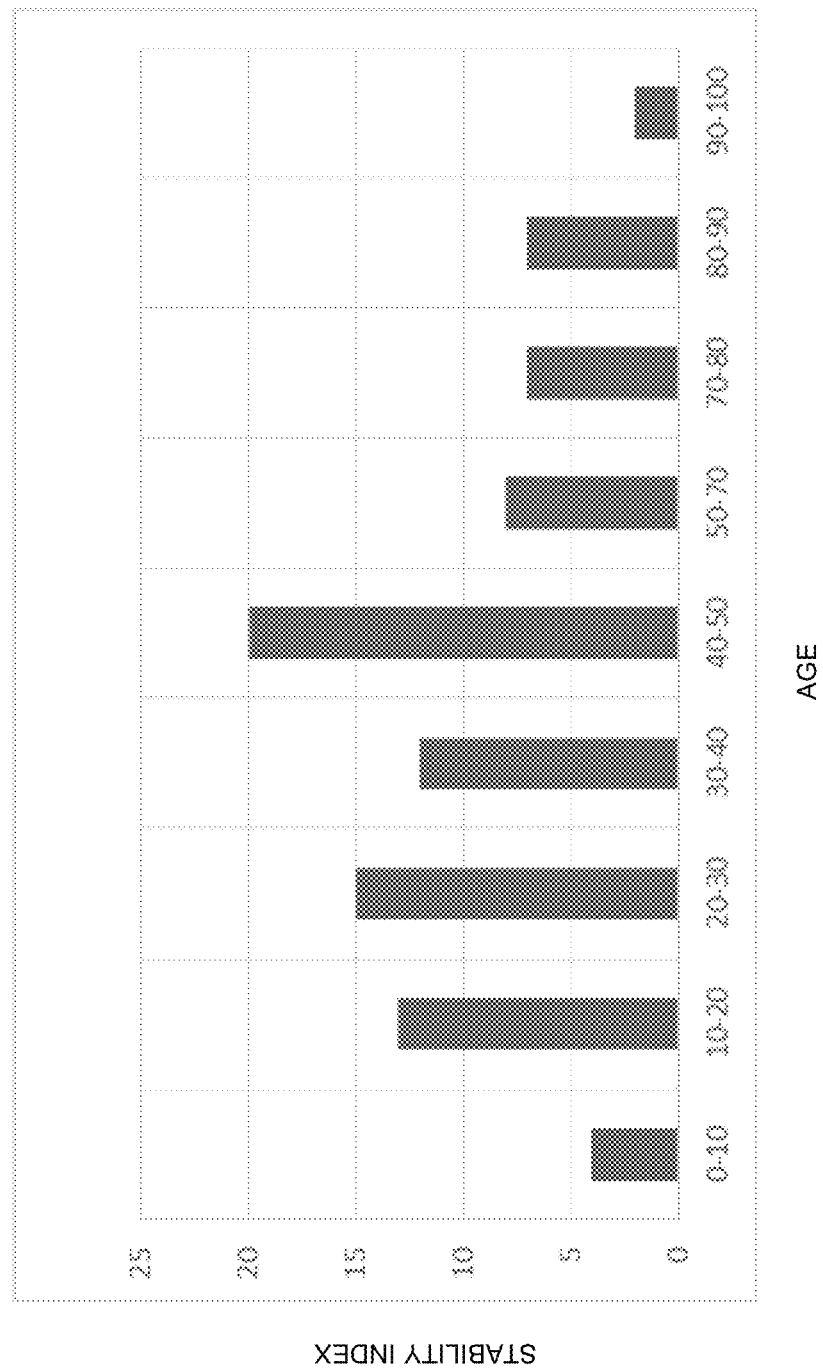
FIG. 7 illustrates the distribution of the stability index over a large population sample, according to one embodiment.

FIG. 7 illustrates the distribution of the stability index over a large population sample, according to one embodiment. More specifically, each data point of the graph can be obtained by averaging the stability indices of a group of individuals of a similar age within the population sample. The stability index of each individual can be computed using the aforementioned energy-analysis method, i.e., by deriving the relationship between the occurrence frequency of the energy peaks and the energy. In addition to the stability index as defined by the ratio between $E_1$ and $E_T$, the balance and/or stability of a complex system may be defined using other criteria, as long as such definition can describe the change (e.g., the shifting) of the occurrence-frequency-over-energy curve. For example, the intersection between the occurrence-frequency-over-energy curve and the line of the reference occurrence, as shown in FIGS. 5A-5B, can also be used to define stability.

In addition to inferring age and health of individuals, the stability analysis can also find applications in many other areas. For example, it can be used to diagnose certain diseases (e.g., Parkinson's), determining the effectiveness of a treatment, or evaluating the fatigue level of athletes after training. Similarly, the stability analysis can also be used to evaluate the performance of certain machineries (such as engines for cars, boats, and planes; wind turbines; etc.) and to evaluate the stability of certain structures (e.g., buildings and bridges). In general, by obtaining motion sensor data and by performing the energy analysis based on the motion sensor data, one can infer useful information regarding the stability of a complex system.

Figure 8:
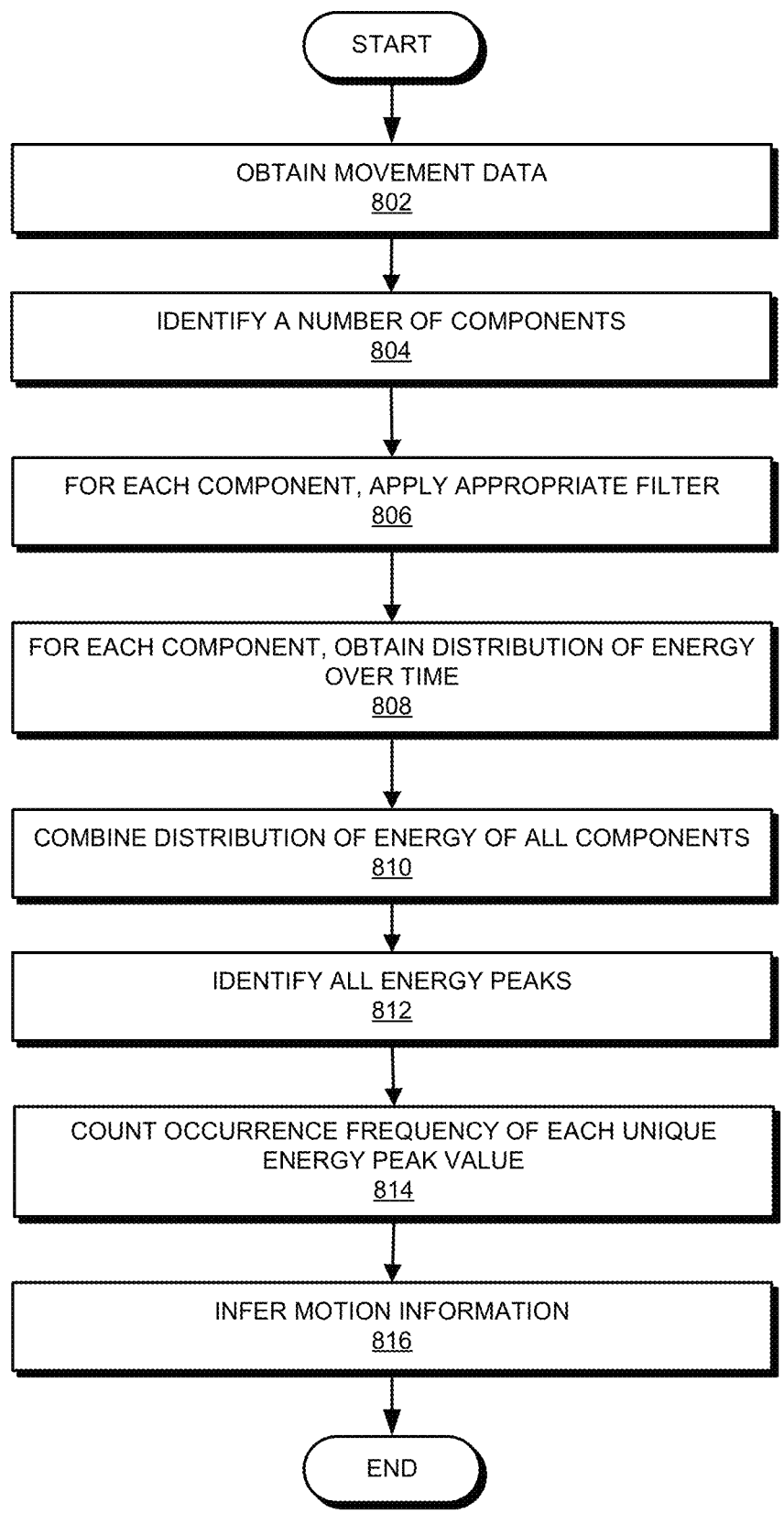
FIG. 8 presents a flowchart illustrating an exemplary motion-analysis process, according to one embodiment.

FIG. 8 presents a flowchart illustrating an exemplary motion-analysis process, according to one embodiment. During operation, the system obtains movement data (e.g., acceleration data) from a motion sensor mounted at the center of gravity of a complex system (operation 802). The motion sensor can include a number of measurement modules capable of measuring different aspects of the movement. The measurement modules can include but are not limited to: a 3-axis accelerometer, a gyroscope, and a magnetometer. The 3-axis accelerometer can provide acceleration information along with orientation information associated with the movement, the gyro scope can provide information associated with the rotation, and the magnetometer can further improve the accuracy of the orientation information. In some embodiments, the movement data can include sensor data over a predetermined duration. For example, a user may be asked to stand still while wearing the sensor and sensor data for a predetermined duration (e.g., 30 seconds) can be extracted and analyzed. The sensor data can be analyzed in real time or offline. The sampling rate of the sensor can be between a few hertz to a few thousand hertz, as long as the sensor sampling rate is sufficiently high for the particular motion being monitored. In some embodiments, the sampling rate of the sensor can be about 100 Hz.

The system can identify a number of components of the sensor data (operation 804). For example, the acceleration data can be decomposed into the linear acceleration data and the angular acceleration data. Moreover, the magnetic field measurement can also be separately obtained. All individual components of the movement data can be directly measured or derived from measurements. For each component, the system can apply an appropriate filter to remove noise and the non-oscillatory motion component (operation 806). More specifically, the system can determine the appropriate frequency range of the filter. For example, the system can determine the frequency range of a noise filter based on the frequency range of the noise. Similarly, depending on the frequency (e.g., a fundamental frequency) associated with the non-oscillatory portion of the motion, the system can apply one or more filters capable of filtering out the motion data associated with the non-oscillatory portion of the motion. For example, for a rotating wind turbine, motion data (e.g., angular acceleration) associated with the rotations can be filtered out. Similarly, for a person walking forwardly, motion data associated with the forward motion can be filtered out.

Subsequently, for each component, the system can obtain the distribution of the motion energy over time (operation 808). To do so, the system can calculate an amount of motion energy expenditure for a series of sampling periods. Depending on the sampling rate of the sensor, a sampling period can be between a few micro seconds and a few seconds (e.g., 10 ms). The total number of sampling periods depending on the duration of the measurement, which can be between a few seconds and a few minutes. The number of data points needs to be sufficiently large in order to obtain statistical significance. The system can then combine the amounts of motion energy from all motion components to obtain the distribution of the total energy of the oscillatory motion over the predetermined duration (e.g., the duration of the measurement) (operation 810).

The system can then identify all energy peaks from the energy distribution data (operation 812) and count the occurrence frequency of each unique energy peak value (operation 814). In some embodiments, the system may also define a threshold value and, if the difference between two energy peaks is smaller than the threshold value, these two energy peaks can be considered to have the same energy value. This threshold value essentially determines the resolution of the energy-analysis system. By counting the occurrence frequency for each unique energy peak value, the system can obtain the distribution of the energy-occurrence frequency over the entire range of those energy peaks (i.e., the energy difference between the highest and lowest peaks).

Based on the distribution of the energy-occurrence frequency over the energy range, the system can infer various types of motion information associated with the complex system (operation 816). In some embodiments, the system can obtain balance and/or stability information associated with the motion of the complex system. For example, the system can compare the distribution of the energy-occurrence frequency of a complex system under test to the distribution of the energy-occurrence frequency of a reference system in order to determine the relative motion properties (e.g., balance or stability) of the complex system. In some embodiments, the system can calculate a stability index and can present such a stability index to the user on a display of a mobile device.

Note that the operations shown in FIG. 8 can also be iterated over additional time intervals. The sensor data can be obtained separately for each time interval. Alternatively, the sensor data can be obtained for a large interval, which can then be divided into smaller intervals, and the motion-analysis operations shown in FIG. 8 can be performed for each smaller interval.

Depending on the application, the motion information associated with the energy occurrence frequency can be used to obtain various results or conclusions that can be presented to the user. For example, the system can compare occurrence frequency of energy peaks within a particular energy range among multiple complex systems (e.g., a group of individuals) in order to determine the health, wellness, fitness, and/or age of the individuals. Moreover, by comparing the distribution of the energy-occurrence frequency before a treatment (or procedure) and the distribution of the energy-occurrence frequency after the treatment (or procedure), the system can evaluate the effectiveness of the treatment (or procedure). Similar approaches can be used to evaluate the performance of sport equipment (e.g., footwear, bicycle, skates, skis, etc.) or machines (e.g., engines, turbines, etc.).

Figure 9:
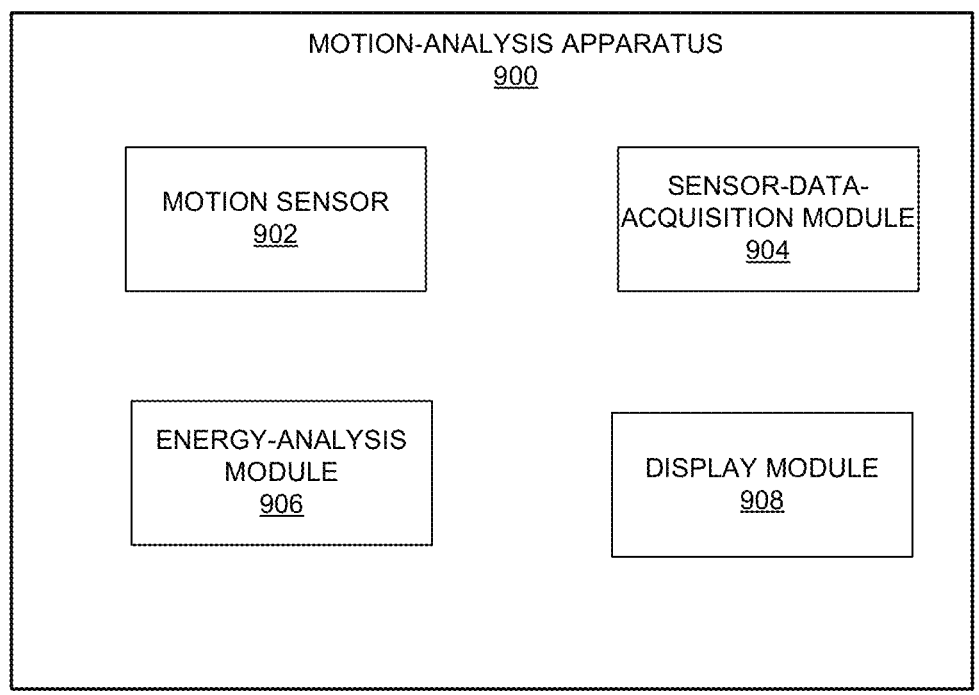
FIG. 9 illustrates an exemplary motion-analysis apparatus, according to one embodiment.

FIG. 9 illustrates an exemplary motion-analysis apparatus, according to one embodiment. Motion-analysis apparatus 900 can include a motion sensor 902, a sensor-data-acquisition module 904, an energy-analysis module 906, and a display module 908.

Motion sensor 902 can include one or more measurement modules, including but not limited to: a 3-axis accelerometer, a gyroscope, and a magnetometer. Sensor-data-acquisition module 804 can obtain motion-measurement data from motion sensor 902. In some embodiments, sensor-data-acquisition module 904 can acquire the motion-measurement data via a wireless link (e.g., WiFi™ or Bluetooth™). Alternatively, sensor-data-acquisition module 904 can acquire the motion-measurement data via a wired link (e.g., peripheral component interconnect express (PCIe) or I²C).

Energy-analysis module 906 can be responsible for performing energy analysis of the motion based on the motion-measurement data. More specifically, based on the acceleration data, energy-analysis module 906 can first compute the distribution of the oscillatory energy of the motion over a time interval and then obtain the distribution of occurrence of the energy peaks over an energy range. In some embodiments, the system can compute, in the log scale, the rate of change of the energy-peak-occurrence frequency as a function of the energy. The distribution of the occurrence of the energy peaks of a complex system exhibits an SOC behavior. By comparing the distributions of the occurrence of the energy peaks between a complex system and a reference system, motion information (e.g., balance and/or stability) of the complex system can be derived. In a further embodiment, energy-analysis module 806 can also correlate the acceleration or force trajectory of a motion with the time-dependent distribution of the energy in order to obtain motion information in the time domain (e.g., predicting a fall risk or a direction of falling).

Display module 908 can be responsible for displaying the motion-analysis results to the user. In some embodiments, display module 908 can display the corresponding relationship between an acceleration or force trajectory of a motion and the time-dependent distribution of the motion energy. Moreover, display module 908 can also display the energy-peak-occurrence-frequency over the energy curve of a complex system. Such a curve can also be displayed along a similar curve of a reference system to allow the user to infer stability and/or balance information associated with the complex system.

Figure 10:
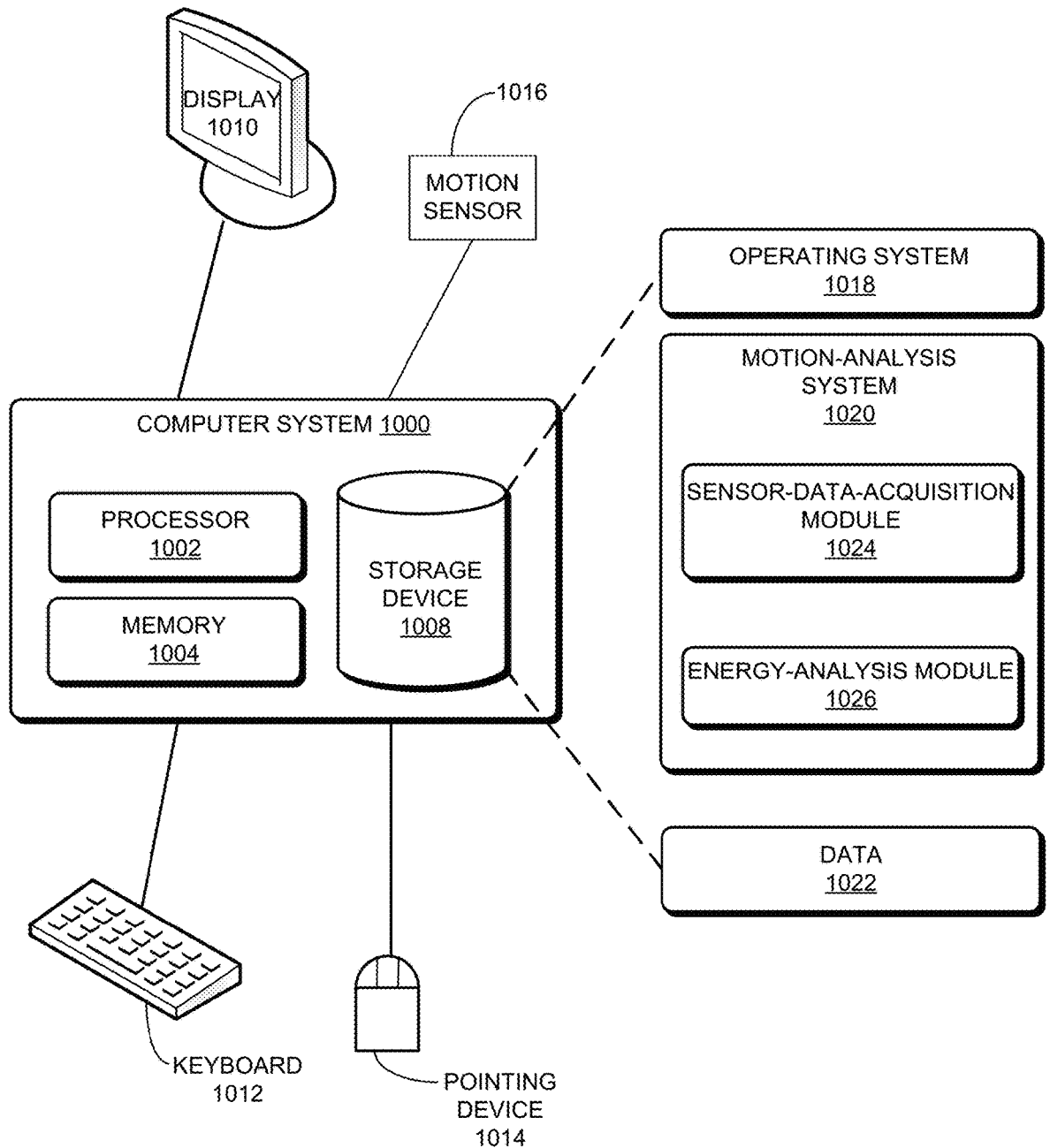
FIG. 10 illustrates an exemplary computer system that facilitates motion analysis, according to one embodiment.

FIG. 10 illustrates an exemplary computer system that facilitates motion analysis, according to one embodiment. In this example, a computer system 1000 includes a processor 1002, a memory device 1004, and a storage device 1008. Furthermore, computer system 1000 can be coupled to a display device 1010, a keyboard 1012, a pointing device 1014, and a motion sensor 1016. Storage device 1008 can store codes for an operating system 1018, a motion-analysis system 1020, and data 1022.

Motion-analysis system 1020 can include instructions, which when executed by processor 1002 can cause computer system 1000 to perform methods and/or processes described in this disclosure. Specifically, motion-analysis system 1020 can include instructions for implementing a sensor-data-acquisition module 1024 and an energy-analysis module 1026.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, methods and processes described herein can be included in hardware modules or apparatus. These modules or apparatus may include, but are not limited to, an application-specific integrated circuit (ASIC) chip, a field-programmable gate array (FPGA), a dedicated or shared processor that executes a particular software module or a piece of code at a particular time, and/or other programmable-logic devices now known or later developed. When the hardware modules or apparatus are activated, they perform the methods and processes included within them.

The foregoing descriptions of various embodiments have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention.

What is claimed is:

1. A method for analyzing a motion of a human user, the method comprising:
    attaching at least one motion sensor substantially near a lower back of the human user;
    performing a motion measurement on the human user using the at least one motion sensor;
    obtaining, by a computer over a wired or wireless interface associated with the at least one motion sensor, movement data of the human user over a time interval from the at least one motion sensor;
    computing, over the time interval, a distribution of energy as a function of time associated with the motion based on the obtained movement data;
    identifying energy peaks based on the distribution of the energy over the time interval;
    determining an occurrence frequency of an energy peak having a unique energy value;
    computing an energy-occurrence-frequency distribution as a function of energy based on the determined occurrence frequencies of energy peaks within a predetermined energy range;
    determining a level of stability associated with the human user based on the computed energy-occurrence-frequency distribution; and
    presenting, on a display associate with the computer, the determined level of stability to the human user.

2. The method of claim 1, further comprising:
    wherein the at least one motion sensor is attached directly behind a lumbosacral joint of the human user; and
    wherein the at least one motion sensor comprises one or more of: a three-axis accelerometer, a gyroscope, and a magnetometer.

3. The method of claim 1, further comprising:
    counting an occurrence of an energy value between two identified energy peaks.

4. The method of claim 1, wherein the movement data comprises acceleration data, and wherein computing the distribution of the energy as a function of time comprises:
    performing a Fourier transform (FT) operation on the acceleration data to obtain a plurality of frequency components of the acceleration;
    computing, for each frequency of a predetermined set of frequencies, a frequency component of the energy; and
    summing the computed frequency components of the energy.

5. The method of claim 1, further comprising:
    obtaining an energy-occurrence-frequency distribution as a function of energy for a reference system.

6. The method of claim 5, wherein determining the level of stability comprises:
    selecting a reference energy-occurrence frequency; and
    comparing energy values corresponding to the reference energy-occurrence frequency for the human user and the reference system.

7. The method of claim 1, wherein determining the level of stability comprises one of:
    computing a stability index based on a ratio between a count of energy occurrences for energies up to a reference energy value and a total count of energy occurrences; and
    computing a distance between upper and lower boundaries of the energy-occurrence-frequency distribution at a reference energy-occurrence frequency.

8. A non-transitory computer-readable storage device storing instructions that when executed by a computer cause the computer to perform a method for analyzing a motion of a human user, the method comprising:
    obtaining, from at least one motion sensor over a wired or wireless interface associated with the at least one motion sensor, movement data of the human user over a time interval-, wherein the at least one motion sensor is attached substantially near a lower back of the human user;
    computing, over the time interval, a distribution of energy as a function of time associated with the motion based on the obtained movement data;
    identifying energy peaks based on the distribution of the energy over the time interval;
    determining an occurrence frequency of an energy peak having a unique energy value;
    computing an energy-occurrence-frequency distribution as a function of energy based on the determined occurrence frequencies of energy peaks within a predetermined energy range;
    determining a level of stability associated with the human user based on the computed energy-occurrence-frequency distribution; and
    presenting, on a display associate with the computer, the determined level of stability to the human user.

9. The non-transitory computer-readable storage device of claim 8,
    wherein the at least one motion sensor is attached directly behind a lumbosacral joint of the human user; and
    wherein the at least one motion sensor comprises one or more of: a three-axis accelerometer, a gyroscope, and a magnetometer.

10. The non-transitory computer-readable storage device of claim 8, wherein the method further comprises:
    counting an occurrence of an energy value between two identified energy peaks.

11. The non-transitory computer-readable storage device of claim 8, wherein the movement data comprises acceleration data, and wherein computing the distribution of the energy as a function of time comprises:

performing a Fourier transform (FT) operation on the acceleration data to obtain a plurality of frequency components of the acceleration;
computing, for each frequency of a predetermined set of frequencies, a frequency component of the energy; and
summing the computed frequency components of the energy.

12. The non-transitory computer-readable storage device of claim 8, wherein the method further comprises:

obtaining an energy-occurrence-frequency distribution as a function of energy for a reference system.

13. The non-transitory computer-readable storage device of claim 12, wherein determining the level of stability comprises:

selecting a reference energy-occurrence frequency; and
comparing energy values corresponding to the reference energy-occurrence frequency for the human user and the reference system.

14. The non-transitory computer-readable storage device of claim 8, wherein determining the level of stability comprises one of:

computing a stability factor based on a ratio between a count of energy occurrences for energies up to a reference energy value and a total count of energy occurrences; and
computing a distance between upper and lower boundaries of the energy-occurrence-frequency distribution at a reference energy-occurrence frequency.

15. An apparatus for analyzing a motion of a human user, comprising:

one or more motion sensors attached substantially near a lower back of the human user and configured to perform a motion measurement on the human user; a processor; and
a storage device storing instructions that when executed by the processor cause the processor to perform a method, the method comprising:
obtaining, from the motion sensors over a wired or wireless interface associate with the motion sensors, movement data of the human user over a time interval;
computing, over the time interval, a distribution of energy as a function of time associated with the motion based on the obtained movement data;
identifying energy peaks based on the distribution of the energy over the time interval;
determining an occurrence frequency of an energy peak having a unique energy value;
computing an energy-occurrence-frequency distribution as a function of energy based on the determined occurrence frequencies of energy peaks within a predetermined energy range; determining a level of stability associated with the human user based on the computed energy-occurrence-frequency distribution; and
presenting, on a display associate with the processor, the determined level of stability to the human user.

16. The apparatus of claim 15, wherein the motion sensors are attached directly behind a lumbosacral joint of the human user, and wherein the one or more motion sensors comprise one or more of: a three-axis accelerometer, a gyroscope, and a magnetometer.

17. The apparatus of claim 15, wherein the method further comprises:

counting an occurrence of an energy value between two identified energy peaks.

18. The apparatus of claim 15, wherein the method further comprises:

obtaining an energy-occurrence-frequency distribution as a function of energy for a reference system.

19. The apparatus of claim 18, wherein determining the level of stability comprises:

selecting a reference energy-occurrence frequency; and
comparing energy values corresponding to the reference energy-occurrence frequency for the human user and the reference system.

20. The apparatus of claim 15, wherein determining the level of stability comprises:

computing a stability factor based on a ratio between a count of energy occurrences for energies up to a reference energy value and a total count of energy occurrences; and
computing a distance between upper and lower boundaries of the energy-occurrence-frequency distribution at a reference energy-occurrence frequency.

* * * * *